United States Patent
Fleshner

(10) Patent No.: US 6,670,392 B2
(45) Date of Patent: Dec. 30, 2003

(54) COMPOSITIONS AND METHODS FOR THE PREVENTION AND TREATMENT OF HUMAN PROSTATE CANCER

(75) Inventor: Neil E. Fleshner, Toronto (CA)

(73) Assignee: Bioadvantex Pharma Inc., Ontario (CA)

( * ) Notice: Subject to any disclaimer, the term of this patent is extended or adjusted under 35 U.S.C. 154(b) by 100 days.

(21) Appl. No.: 09/828,405

(22) Filed: Apr. 6, 2001

(65) Prior Publication Data

US 2003/0018066 A1 Jan. 23, 2003

(51) Int. Cl.$^7$ ................. A61K 31/355; A61K 33/04
(52) U.S. Cl. ..................................... 514/458; 424/702
(58) Field of Search ........................... 514/458; 424/702

(56) References Cited

U.S. PATENT DOCUMENTS

| | | | | |
|---|---|---|---|---|
| 3,928,578 A | * | 12/1975 | Burns et al. | 424/702 |
| 5,888,552 A | * | 3/1999 | Bounous et al. | 424/535 |
| 6,090,414 A | * | 7/2000 | Passwater et al. | 424/702 |
| 6,197,309 B1 | * | 3/2001 | Wheeler | 424/641 |
| 6,299,896 B1 | * | 10/2001 | Cooper et al. | 424/400 |
| 2001/0043925 A1 | * | 11/2001 | Hsia et al. | 424/93.51 |
| 2002/0012715 A1 | * | 1/2002 | Soldati | 424/766 |
| 2002/0094323 A1 | * | 7/2002 | Hellstrand et al. | 424/85.1 |

FOREIGN PATENT DOCUMENTS

| | | | | |
|---|---|---|---|---|
| CH | 654206 | * | 2/1986 | 424/702 |
| WO | WO 01/26668 A1 | | 4/2001 | |

OTHER PUBLICATIONS

Chan et al, Semin. Cancer Biol., vol. 8, #4, pp. 263–273, (abstract), 1998.*
J. Natl. Cancer Inst., vol. 19, #16, pp. 1219–1224 (abstract) 1998.*
Fleshner et al, Urology, vol. 57, #4 suppl 1, pp. 90–94 (abstract) 2001.*
Holzlsour et al, J. Natl. Cancer Inst., vol. 20, #24, pp. 2018–2023 (abstract) 2000.*
Kelloff et al, Annals New York Academy of Science, pp. 1–13.*
Azzi A, Breyer I, Feher M, Pastori M, Ricciarelli R, Spycher S, Staffieri M, Stocker A, Zimmer S, Zingg JM, "Specific Cellular Responses to Alpha–Tocopherol," J Nutr (Jul. 2000) 130(7): 1649–52.
Brigelius–Flohe R, Traber MG, "Vitamin E: Function and Metabolism," FASEB (1999) 13: 1145–1155.
Fleshner NE, "Vitamin E Inhibits the High–Fat Diet Promoted Growth of Established Human Prostrate LNCaP Tumors in Nude Mice," J Urol (1999) 161: 1651–1654.
Hartwell L, "Defects in a Cell Cycle Checkpoint May Be Responsible for the Genomic Instability of Cancer Cells," Cell (1992) 71: 543–546.
Heinonen OP, et al., "Prostate Cancer and Supplementation with Alpha–Tocopherol and Beta–Carotene: Incidence and Mortality in a Controlled Trial," J Natl Cancer Inst. (1998) 90: 440–446.
Helzlsouer KJ, Comstock GW, Morris JS et al., "Selenium, Lycopene, A–Tocopherol, B–Carotene, Retinol and Subsequent Bladder Cancer," Cancer Res(1989) 49: 6144–6148.
Hunter DJ, Morris JS, Stampfer MJ et al., "A Prospective Study of Selenium Status and Breast Cancer Risk," JAMA (1990) 264: 1128–1131.
La Thangue NB, "Introduction: Cell Cycle Regulation and Cancer," Seminars in Cancer Biol. (1995) 6: 61–62.
Levander OA, "Scientific Rationale for the 1989 Recommended Dietry Allowance for Selenium," Perspect Pract (1991) 91: 1572–1576.
Morgan DO, "Cyclin–Dependent Kinases: Engines, Clocks and Microprocessors," Ann. Rev. Dev. Biol. (1997) 13: 261–291.
Pagano M et al., "Role of Ubiquitin–Proteasome Pathway in Regulating Abundance of the Cyclin–Dependent Kinase Inhibitor p27," Science (1995)269: 682–685.
Parker Si, et al., "Cancer Statistics 1997," CA Cancer J Clin (1997) 47: 5–27.
Polyak C et al., "p27Kip1, a Cyclin–cdk Inhibitor, Links Transforming Growth Factor–b and Contact Inhibition to Cell Cycle Arrest," Genes Dev. (1994) 8: 9–22.
Pryor WA, "Vitamin E and Heart Disease: Basic Science to Clinical Intervention Trials," Free Radic Biol Med (Jan. 1, 2000) 28(1): 141–64.
Rao AV, Fleshner N, Agarwal S . . , "Serum and Tissue Lycopene and BioMarkers of Oxidation in Prostate Cancer Patients: A Case–Control Study", Nutr Cancer (1999) 33(2): 159–64.
Ripple Mo, et al., "Prooxidant–antioxidant Shift Induced by Androgen Treatment of Human Prostate Carcinoma Cells," J Natl Cancer Inst. (1997) 89: 40–48.
Sherr CJ et al., Roberts JM, "CDK inhibitors: positive and negative regulators of G1–phase progression", Genes Dev. (1999) 13: 1501–1512.

(List continued on next page.)

Primary Examiner—James H. Reamer
(74) Attorney, Agent, or Firm—Eugene C. Rzucidlo

(57) ABSTRACT

The invention provides a composition and method for the prevention or treatment of mammalian prostate carcinoma using Vitamin E or Vitamin E derivatives or Vitamin E analogs and selenium or selenium salt or selenium derivatives in a combined or an uncombined form, alone or in combination with traditional therapies. The invention also provides a composition and method for the prevention or treatment of mammalian prostate carcinoma using Vitamin E or Vitamin E derivatives or Vitamin E analogs and selenium or selenium salt or selenium derivatives in a combined or an uncombined form, alone or in combination with traditional therapies to increase the levels of intracellular p21 and/or p27.

16 Claims, 12 Drawing Sheets

OTHER PUBLICATIONS

Solomon MJ, "Activation of the Various Cyclin/cdk2 Proteins," Curr. Opin. Cell. Biol. (1993) 5: 180–186.

Tslhlias J et al., "Involvement of p27Kip1 in G1 Arrest by High–Dose 5a–Dihydrotestosterone in LNCaP Human Prostate Cancer Cells," Oncogens (2000) 19: 670–679.

Van den Brandt PA, Goldbohn RA, Bode P et al., "A Prospective Study on Toenail Selenium Levels and Risk of Gastrointestinal Cancer,"J Natl Cancer Inst (1993)85: 224–229.

Van Den Brandt PA, Goldbohn RA Bode P et al., "A Prospective Study On Selenium Status And The Risk Of Lung Cancer," Cancer Res. (1993) 53: 4860–4865.

Willett WE, Polk BF, Morris JS et al., "Prediagnostic Serum Selenium and Risk of Cancer," Lancet (1983) 2: 130–134.

* cited by examiner

| Vit E | − | − | + | + |
| Time (h) | 0 | 0 | 48 | 48 |
| p27 | − | + | − | + |
Cyclin E 
cdk2 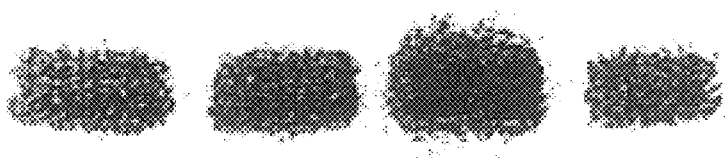
p27 
FIG. 5

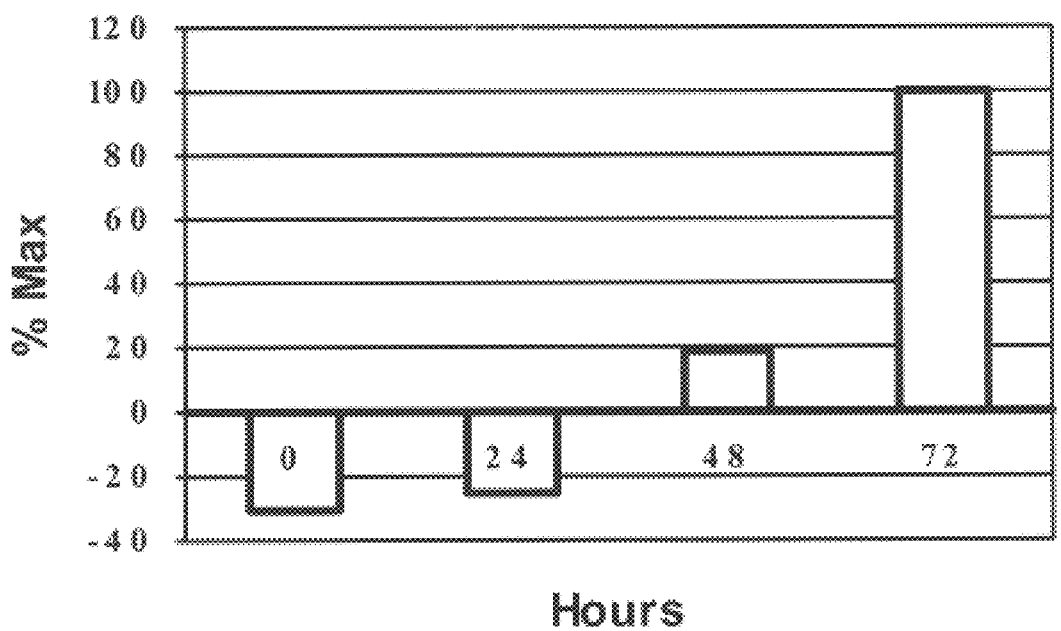

FACS analysis on Vitamin E and Selenium treated LNCaP

Cyclin E Immune Complexes
(LNCaP)

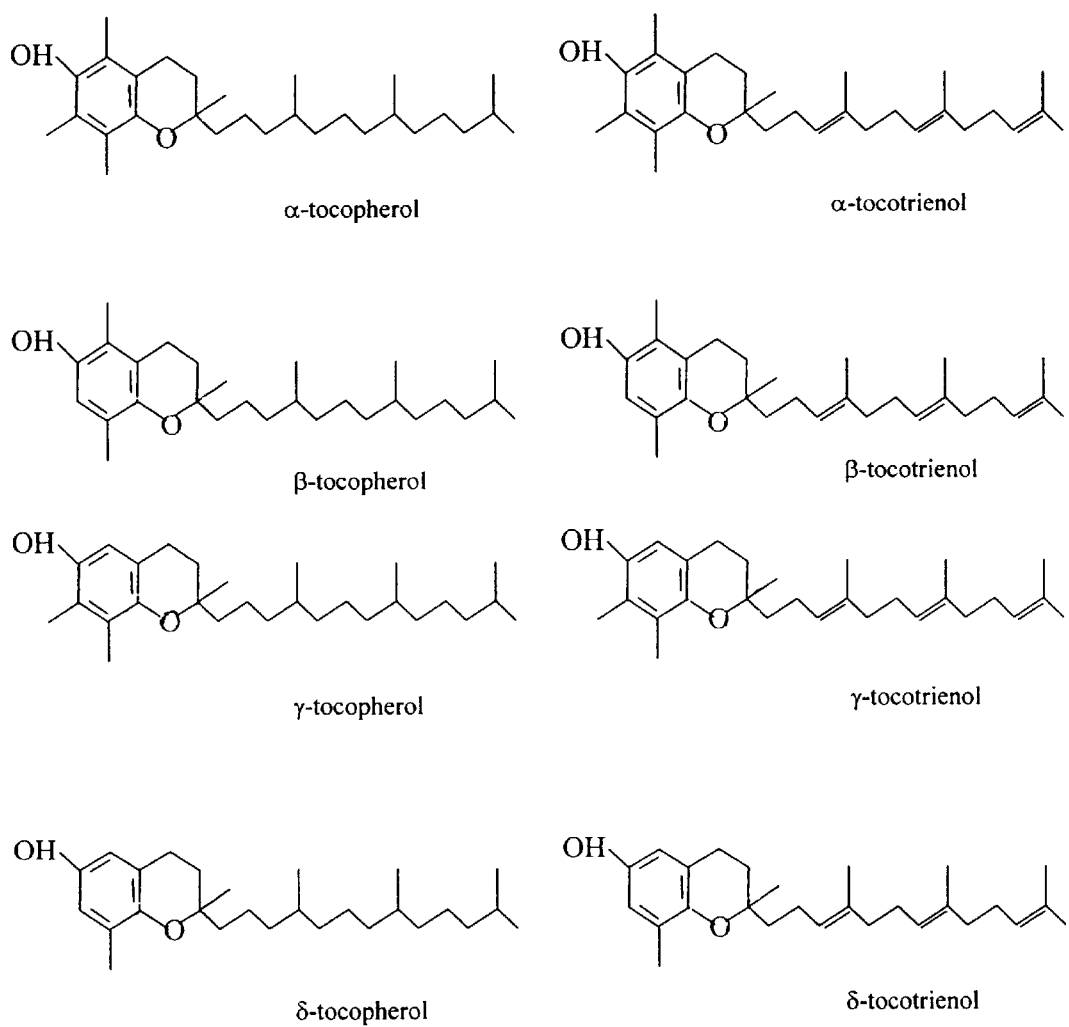
FIGURE 13. VITAMIN E FORMS

COMPOSITIONS AND METHODS FOR THE PREVENTION AND TREATMENT OF HUMAN PROSTATE CANCER

FIELD OF THE INVENTION

The present invention relates to a method and an adjunct or complement composition to traditional therapies for the treatment or prevention of prostate cancer in mammals as well as a method and composition useful for the prevention of the onset of prostate cancer in mammals. The composition of this invention comprises of Vitamin E or a Vitamin E derivative in combination with selenium either in combined or uncombined form in amounts which provide preventive and therapeutic effects with mammalian prostate carcinoma.

BACKGROUND OF THE INVENTION

Prostate cancer is the most common cancer in mammals, especially among human males in North America, and it is the second leading cause of cancer death in men in the Western countries. See Parker S I, et al, "Cancer Statistics 1997," *CA Cancer J Clin* (1997) 47:5–27. Various factors such as an unknown etiology, variable pathology, an intricate relationship to endocrine factors, and anaplastic progression contribute to the complexity of this disease.

Evidence from epidemiologic, clinical and laboratory studies supports the concept that a complex interaction between the host antioxidant defense system and dietary antioxidants may participate in the origin and progression of prostate cancer, as well as other forms of cancer. For example, supplemental consumption of the antioxidant Vitamin E has been associated with a reduction of about one-third in mortality from prostate cancer. See, e.g., Fleshner N E, "Vitamin E Inhibits the High-Fat Diet Promoted Growth of Established Human Prostate LNCaP Tumors in Nude Mice," *J Urol* (1999) 161: 1651–1654. Considerable interest has also been generated in the possible role of trace elements in cancer prevention and intervention. An indirect correlation between the levels of bioavailable selenium in the human environment and cancer mortality has also been reported. See Hunter D J, Morris J S, Stampfer M J et al., "A Prospective Study of Selenium Status and Breast Cancer Risk," *JAMA* (1990) 264: 1128–1131; See Van den Brandt P A, Goldbohn R A, Bode P et al., "A Prospective Study on Toenail Selenium Levels and Risk of Gastrointestinal Cancer," *J Natl Cancer Inst* (1993) 85: 224–229; See Van Den Brandt P A, Goldbohn R A, Bode P et al., "A Prospective Study On Selenium Status And The Risk Of Lung Cancer," *Cancer Res* (1993) 53: 4860–4865; See Helzlsouer K J, Comstock G W, Morris J S et al., "Selenium, Lycopene, A-Tocopherol, B-Carotene, Retinol and Subsequent Bladder Cancer," *Cancer Res* (1989) 49: 6144–6148; See Willett We, Polk B F, Morris J S et al, "Prediagnostic Serum Selenium and Risk of Cancer," *Lancet* (1983) 2: 130–134; See Levander O A, "Scientific Rationale for the 1989 Recommended Dietary Allowance for Selenium," *Perspect Pract* (1991) 91: 1572–1576. Accumulating evidence suggests that in many models of experimental carcinogenesis, supplementation of the diet with sodium selenite results in a decrease in the incidence of chemical carcinogen-induced carcinomas. See Heinonen O P, et al., "Prostate Cancer and Supplementation with Alpha-Tocopherol and Beta-Carotene: Incidence and Mortality in a Controlled Trial," *J Natl Cancer Inst.* (1998) 90: 440–446.

Epidemiological data and prior research therefore suggests that micronutrient ingestion and diet play a pivotal role in prostate carcinogenesis. Androgen has also been shown to contribute to prostate carcinogenesis. See Ripple M O, et al., "Prooxidant-Antioxidant Shift Induced by Androgen Treatment of Human Prostate Carcinoma Cells," *J Natl Cancer Inst.* (1997) 89: 40–48. The link between diet and the androgens may be oxidative stress. This process is caused by a host of reactive oxygen species which can trigger carcinogenesis. Previous research has found that exogenous androgen increases oxidative stress in human prostate cancer cell lines. See Fleshner, *J Urol.* (1995) 161: 1651–1654.

The cell cycle clock orchestrates the progression of cells through growth and division cycles. Thus it determines whether a cell continues its proliferation or withdraws and enters a state of quiescence. Thus, DNA replication and mitosis are controlled by the activation of S phase- and M phase-specific cyclin-dependent protein kinases (CDKs), respectively. The catalytic subunits of CDKs are active only when complexed with their specific regulatory subunits, termed cyclins. The CDKs control the various cellular processes through phosphorylation of the appropriate substrates within the cell. See Solomon M J, "Activation of the Various Cyclin/cdk2 Proteins," *Curr. Opin. Cell Biol.* (1993) 5: 180–186. The cyclins guide, bind and direct CDKs to appropriate substrates during various phases of the cell cycle thereby dictating where and when these substrates will become phosphorylated. See Hartwell L, "Defects in a Cell Cycle Checkpoint May Be Responsible for the Genomic Instability of Cancer Cells," *Cell* (1992) 71: 543–546. Other important components are the CDK inhibitors (CKIs), such as p21 and p27, that block the action of specific cyclin-CDK complexes. This prevents cell proliferation thus forcing it to enter a state of quiescence, called the $G_0$ phase. See Sherr C J et al, *Genes Dev.* (1999) 13: 1501–1512.

Uncontrolled cell proliferation is the hallmark of cancer. Tumor cells contain or acquire damaged genes that directly regulate their cell cycle. Like other types of cancer, prostate cancer is associated with loss of cell cycle control, resulting in unregulated growth of cells. The precise mechanism by which this occurs is still unknown. See La Thangue N B, "Introduction: Cell Cycle Regulation and Cancer," *Seminars in Cancer Biol.* (1995) 6: 61–62. Cell cycle arrest is mediated by the CKIs p27 and p21. See Tslhlias J et al, "Involvement of p27Kip1 in $G_1$ Arrest by High-Dose 5α-Dihydrotestosterone in LNCaP Human Prostate Cancer Cells," *Oncogenes* (2000) 19: 670–679.

The basis of cell cycle control machinery is comprised of regulatory cyclin subunits complexed to catalytic serine/threonine CDK subunits that phosphorylate substrates in a cell cycle specific fashion. See, e.g., Morgan D O, "Cyclin-Dependent Kinases: Engines, Clocks and Microprocessors," *Ann. Rev. Dev. Biol.* (1997) 13: 261–291. Activation of CDK2 by cyclin E in late $G_1$ at/near the $G_1$ restriction point and by cyclin A at the $G_1$-S phase transition, and cyclin B activation of CDK2 at the $G_2$/M phase transition, suggests the involvement of these cyclin-CDK complexes at specific cell cycle regulatory checkpoints. Id. It is known that p21, a cyclin-dependent kinase inhibitor, can induce cell cycle arrest in $G_1$ and/or $G_2$ by inhibiting kinase activity. Additionally, p27 is regulated by a number of mitogenic and growth inhibitory cytokines and by contact inhibition. See Polyak C et al., "p27Kip1, a Cyclin-cdk Inhibitor, Links Transforming Growth Factor-β and Contact Inhibition to Cell Cycle Arrest," *Genes Dev.* (1994) 8: 9–22. Although growth arrest is not always associated with increased p27 protein levels, id., it is an important mediator of $G_1$ arrest because it acts during $G_0$ and early $G_1$ phase of the cell cycle and inhibits cyclin D1-CDK4 and cyclin E-CDK2 complexes. See Pagano M et al., "Role of Ubiquitin-Proteasome Pathway in Regulating Abundance of the Cyclin-Dependent Kinase Inhibitor p27,"*Science* (1995) 269: 682–685.

Although the anti-carcinogenic effects of Vitamin E and selenium have been noted and studied, there has not been a disclosure for the use of a combination of these two materials for the prevention and/or treatment of mammalian prostate carcinoma. Furthermore, while there are other agents available for chemotherapy of tumors, and other invasive treatment options exist for prostate cancer such as removal of the cancerous prostate or placement of a radioactive seed designed to shrink the tumor, it would be more desirable to provide a composition useful as an adjunct or complement to traditional therapies of low toxicity to a patient which will serve as an anti-carcinogenic agent, especially for prostate cancer. Alternatively, it is desirable to provide compositions which increase levels of p21 and/or p27, as well as other CDK-inhibitors to prevent and treat prostate cancer in mammals.

SUMMARY OF THE INVENTION

An object of this invention is to provide a composition and method which may be used to treat or prevent prostate carcinoma in mammals.

A further object of this invention is to provide a composition comprising Vitamin E or Vitamin E derivatives or Vitamin E analogs and selenium or a selenium salt or selenium derivative in uncombined or combined form in which this composition exhibits enhanced anticarcinogenic properties, especially for the prevention or treatment of mammalian prostate carcinoma.

Another object of the invention is to provide a method and an adjunct or complement composition to traditional therapies for the treatment or prevention of the onset of prostate cancer in mammals.

A still further object of this invention is to provide a method and a composition which inhibit the formation of cyclin-CDK protein complexes, via p21 or p27 upregulation, for the prevention and treatment of mammalian prostate carcinoma.

FACS analysis of LNCaP (a) and PC3 (b) cells treated with 20 μg/ml of Vitamin E: Cells were harvested and prepared for FACS analysis at various time intervals after the addition of Vitamin E to the culture medium. $G_1$ arrest was seen in LNCaP and $G_2$/M arrest in PC3.

Figure 2A:
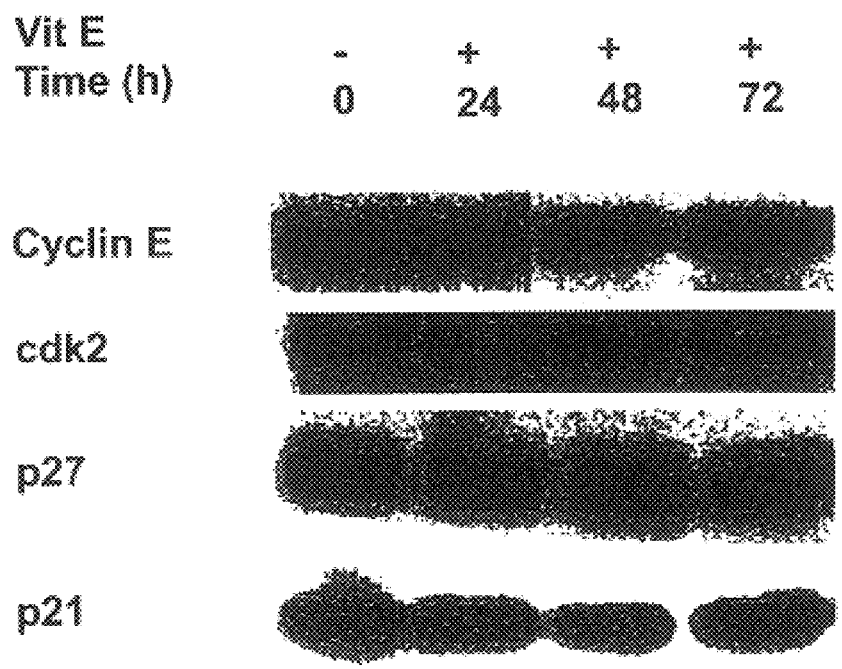

FIGS. 2*a* & *b*

Cell cycle regulators during arrest by Vitamin E: Cells were harvested at the indicated time intervals after the addition of Vitamin E to the culture medium. Lysates were prepared and resolved using SDS-PAGE (a) LNCaP (b) PC3. Proteins were detected by immunoblotting with the indicated antibodies.

Figure 3A:
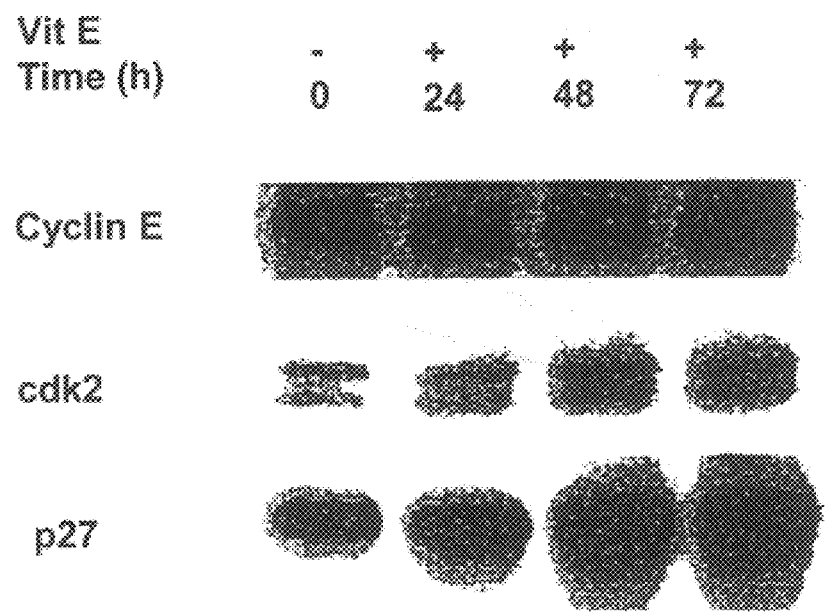

FIGS. 3*a* & *b*

(a) Cyclin E immune complexes (LNCaP): Cells were recovered at various time intervals after addition of Vitamin E to the culture medium. Cyclin E was immunoprecipitated, complexes resolved by SDS-PAGE and immunoblots were reacted with antibodies to detect associated proteins. (b) Cyclin E-associated p27 was quantitated by densitometry from the blots in (a) above. LNCaP cells show a three fold increase in cyclin E-bound p27.

Figure 4A:
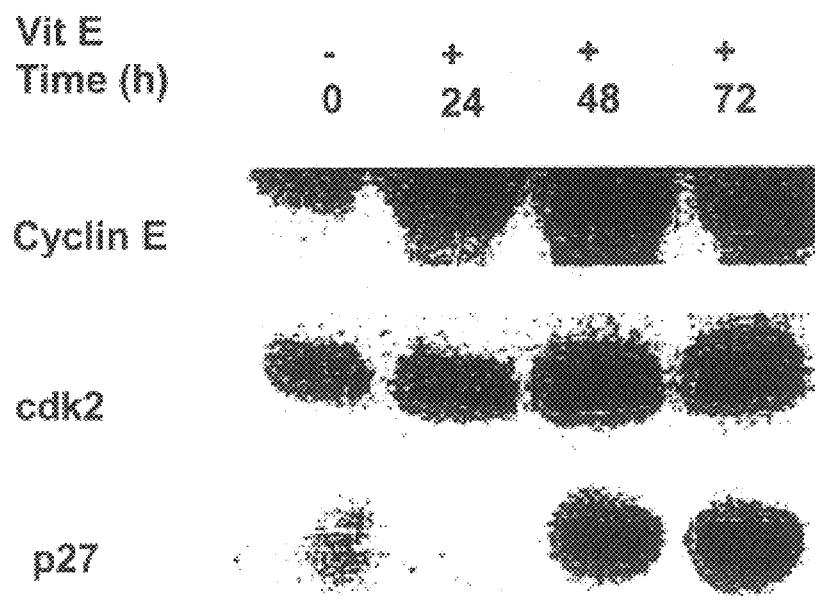

FIGS. 4*a* & *b*

(a) Cyclin E immune complexes (PC3): Cells were recovered at intervals after addition of Vitamin E to the culture media. Cyclin E was immunoprecipitated, complexes resolved by SDS-PAGE and immunoblots were reacted with antibodies to detect associated proteins. (b) Cyclin E associated p27 was quantitated by densitometry from the blots in (a) above. PC3 cells show a six fold increase in cyclin E-bound p27.

FIG. 5

Vitamin E causes increase in the levels of p27 that saturates target cyclin E/cdk2: p27 was serially immunodepleted from LNCaP cell lysates collected at 48 hrs where maximum inhibition was observed after addition of Vitamin E. Cyclin E-associated protein was assayed before and after p27 immunodepletion from 0 and 48 hr samples.

FIG. 6

(a) Dot plot showing the uptake of BrdU and PI in asynchronously growing LNCaP and PC3. (b) Decreased BrdU uptake indicating arrest of DNA synthesis after 72 hours of treatment with 20 μg/ml of Vitamin E.

Figure 7A:
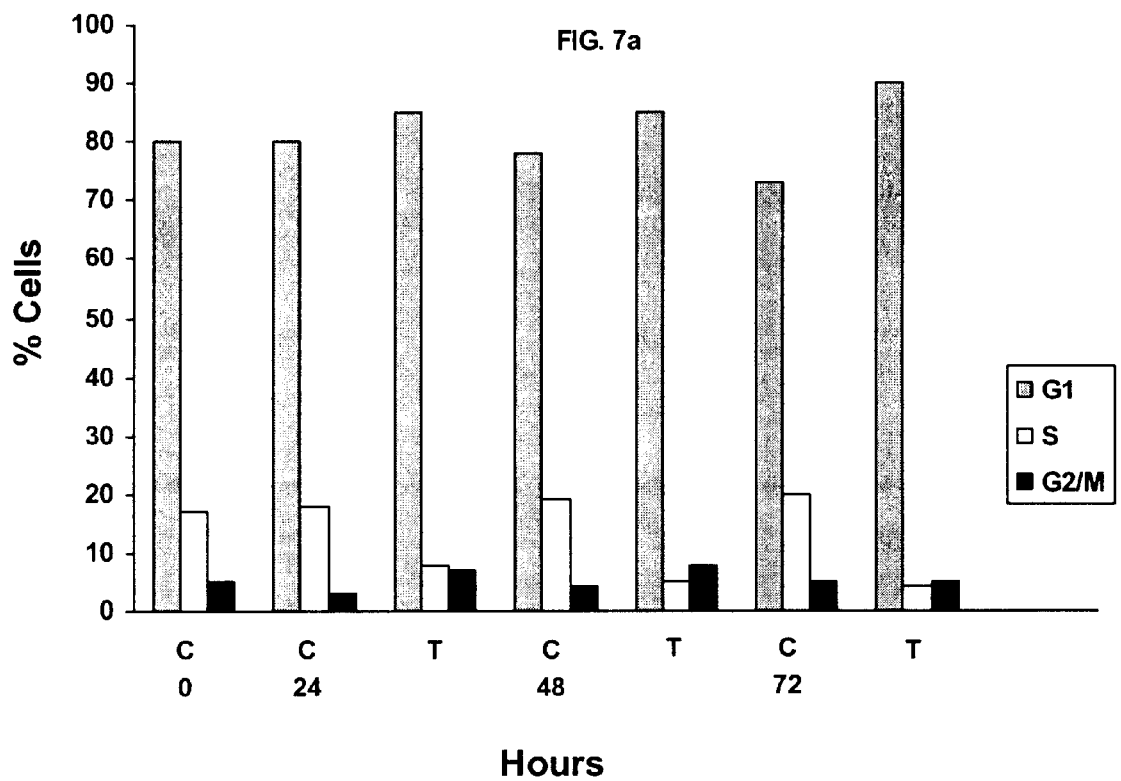
Figure 7B:
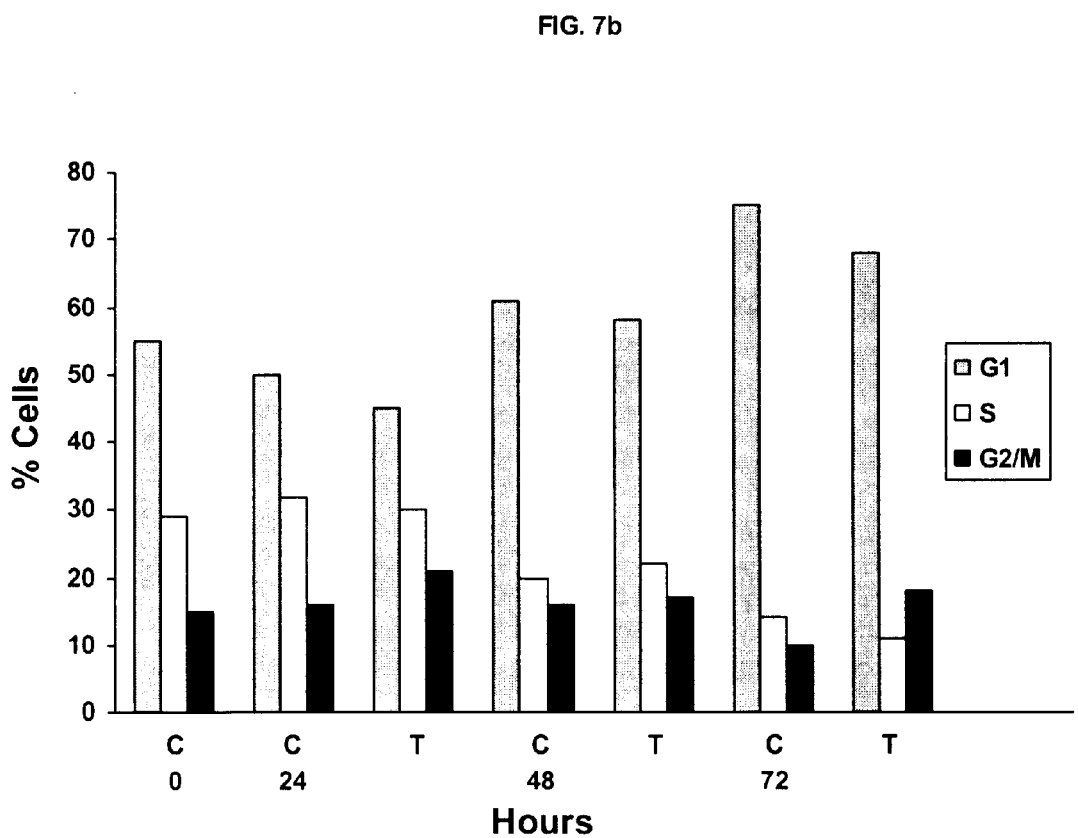

FIGS. 7*a* and 7*b*

FACS analysis of LNCaP (a) and PC3 (b) cells treated with 30 μg of selenium: Cells were harvested and prepared for FACS analysis at various time intervals after the addition of Selenium to culture medium. $G_1$ arrest was seen in LNCaP.

Figure 8A:
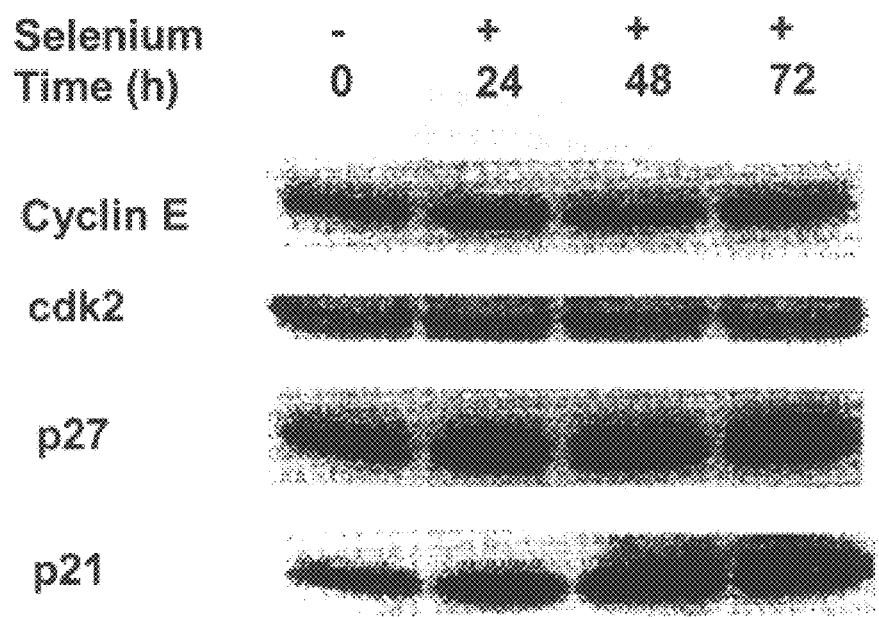
Figure 8B:
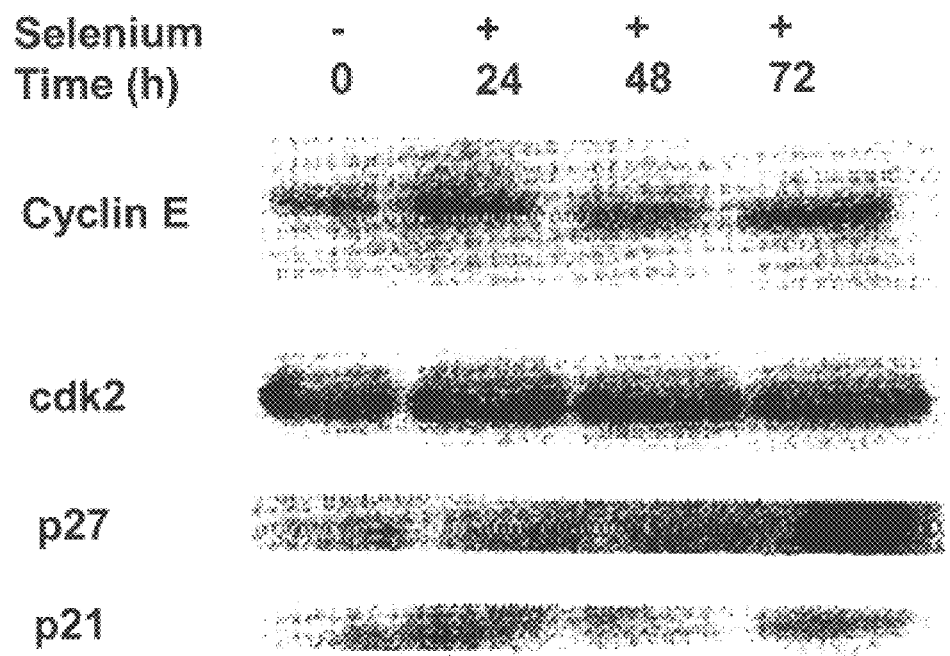

FIGS. 8*a* and 8*b*

Cell cycle regulators during arrest by selenium: Cells were harvested at the indicated time intervals after the addition of Selenium to the culture medium. Lysates were prepared and resolved using SDS-PAGE (a) LNCaP (b) PC3. Proteins were detected by immunoblotting with the indicated antibodies.

Figure 9A:
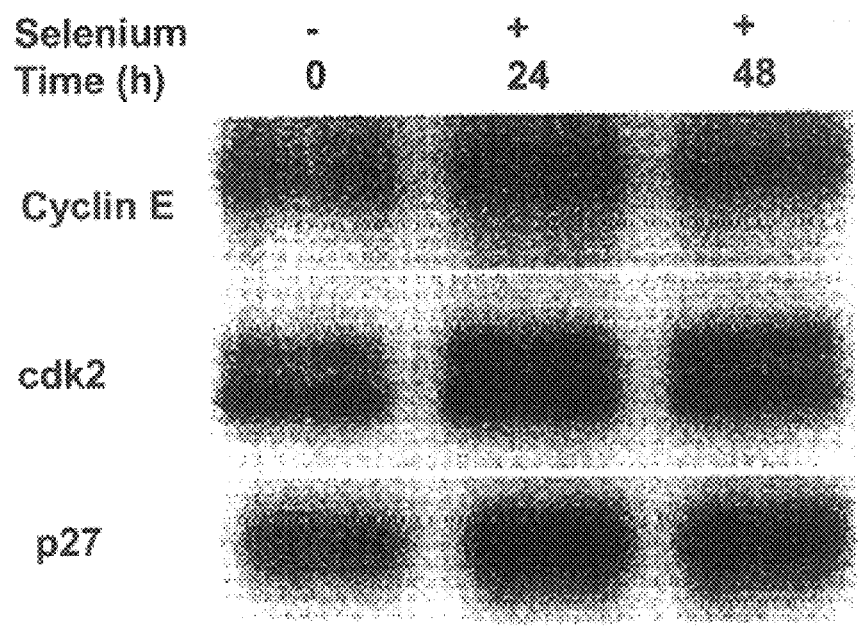
Figure 9B:
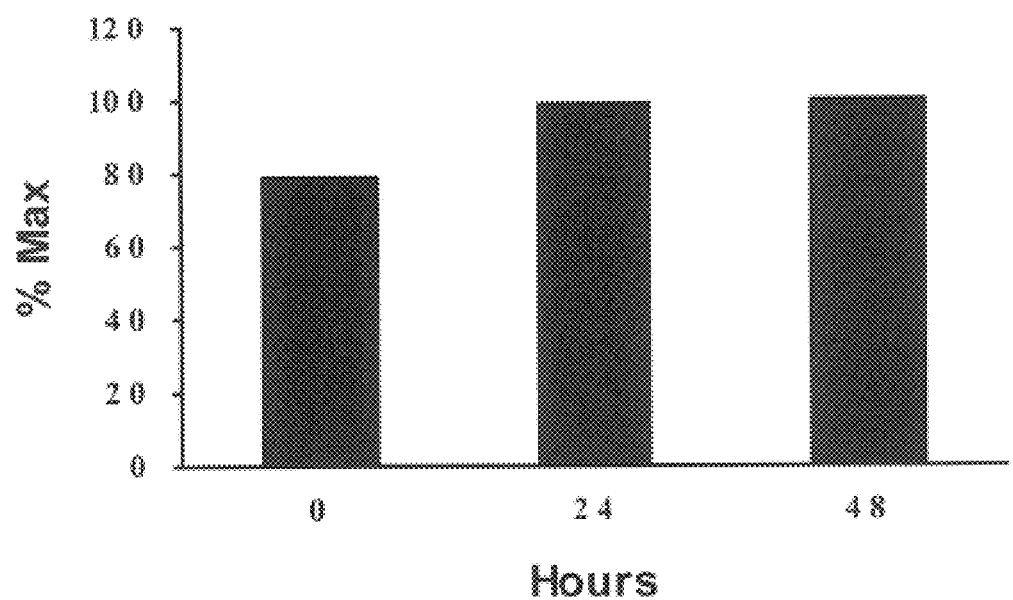

FIGS. 9*a* and 9*b*

(a) Cyclin E immune complexes (LNCaP): Cells were recovered at various time intervals after addition of selenium to the culture medium. Cyclin E was immunoprecipitated, complexes resolved by SDS-PAGE and immunoblots were reacted with antibodies to detect associated proteins. (b) Cyclin E-associated p27 was quantitated by densitometry from the blots in (a) above. LNCaP cells show an increase in cyclin E-bound p27.

FIGS. 10*a* and 10*b*

(a) Cyclin E immune complexes (PC3): Cells were recovered at various time intervals after the addition of selenium to the culture medium. Cyclin E was immunoprecipitated, complexes resolved by SDS-PAGE and immunoblots were reacted with antibodies to detect associated proteins. (b) Cyclin E associated p27 was quantitated by densitometry from the blots in (a) above. PC3 cells show no detectable levels of cyclin E-bound p27 upto 72 hours after treatment.

FIG. 11

FACS analysis of LNCaP cells treated with 20 μg/ml of Vitamin E and 30 μg/ml of selenium. Cells were harvested and prepared for FACS analysis at various time intervals after addition of the micronutrients to the culture medium. Synergistic effects are noted with virtual cell cycle arrest at 72 hours.

FIG. 12

Cell cycle regulators during arrest by combination Vitamin E and selenium in LNCaP cells. Cells were harvested at various time intervals after exposure. Lysates were prepared and resolved by SDS-PAGE. Proteins were detected by immunoblotting with the indicated antibodies. p27 upregulation is noted.

FIG. 13 shows chemical formulas of illustrative Vitamin E derivatives.

DETAILED DESCRIPTION OF THE INVENTION

The method of this invention is the delivery of a composition comprising Vitamin E or Vitamin E derivatives or analogs and selenium or a selenium salt or selenium derivative in combined or uncombined form, at levels of low toxicity to the consumer, to those mammals who have been diagnosed with mammalian prostate carcinoma or those mammals who wish to prevent such carcinoma. Alternatively, the method of this invention is the delivery of a composition of an admixture of agents which inhibit the formation of cyclin-CDK protein complexes, via p21 or p27 upregulation, for the prevention and treatment of mammalian prostate carcinoma.

Laboratory Studies and the Mechanism of Anti-Cancer Action of Vitamin E and Selenium Studies were done to determine whether antioxidants like Vitamin E and bioavailable selenium might be mediating their effects by inducing cell cycle arrest at $G_1/S$ phase in human prostate cancer cell lines through the modulation of CDK inhibitors.

Experimental Methods

Two established human prostate cancer cell lines, LNCaP (androgen responsive) and PC3 (androgen independent), were obtained from the American Type Culture Collection (Rockville, Md.). The LNCaP cells were cultured in RPMI 1640 medium (Gibco BRL, Grand Island, N.Y.), supplemented with 10% Fetal Bovine Serum (FBS) and 100 IU/ml Penicillin and 100 µg/ml Streptomycin, at 37° C. in a humidified atmosphere of 5% $CO_2$ in air. The PC3 cells were cultured in DMEM/F12 medium with 10% FBS and antibiotics. Both sets of cell cultures were grown to 80% confluence in 10 cm tissue culture plates and split 1:8.

One set of LNCaP and PC3 cell cultures were treated with Vitamin E [α-Tochopherol Succinate reconstituted in 95% ethanol] and added to the cultures at a concentration of 20 µg/ml. A second set of LNCaP and PC3 cell cultures were treated with selenium [L-selenomethionine reconstituted in 0.005N HCl] and added to the cultures at a concentration of 30 µg/ml. Controls received the vehicle alone. Treatment was started after 48 hours of attachment. The experimental design was up to 72 hours in culture prior to recovery for flow cytometry and protein analysis.

Cells were pulse labeled with 10 mM bromodeoxyuridine (BrdU) for 2 hours with or without prior treatment of Vitamin E or selenium to asynchronously growing cells. Cells were then harvested, fixed with 70% ethanol, treated with 0.1% HCl and heated for 10 min. at 90° C. to expose the labeled DNA. Cells were stained with anti-BrdU conjugated FITC (Becton Dickinson) and counterstained with propidium iodide. Cell cycle analysis was carried out on a Becton-Dickinson FACScan, using Lysis II software. Cells were then lysed in ice cold NP-40 lysis buffer (0.1% NP-40, 50 nm Tris pH 7.5, 150 mM NaCl, 1 mM phenylmethylsulfonylfluoride, and 0.02 mg/ml each of aprotinin, leupepsin and pepstatin). Lysates were sonicated and clarified by centrifugation. Proteins were quantitated by Bradford analysis and 20–100 µg protein per lane resolved by SDS-polyacrylamide gel electrophoresis (SDS-PAGE). Transfer and blotting was carried out and proteins detected by electrochemiluminescence (ECL). Densitometry was performed using the Molecular Dynamics Imaging system and Image Quant software to quantitate the relative amounts of p27 protein detected on Western Blots. For the detection of cyclin E-associated proteins by immunoprecipitation-Western analysis (IP-Western), cyclin E was immunoprecipitated from 200 µg protein lysates, complexes resolved, blotted and blots reacted with cyclin E, CDK2, p21 and p27 antibodies. For immunodepletion of p27, p27 was serially immunoprecipitated (three times) from 200 µg protein lysates and then cyclin E immunoprecipitated from the p27-depleted lysates. The amounts of immunoprecipitable cyclin E protein, associated CDK2 and p27 protein prior to and after p27 immunodepletion were compared using IP-Western blotting.

The antibodies used in the immunoblotting experiments were: β-actin mouse monoclonal from Sigma Laboratories; cyclin E mouse monoclonal E172 for immunoprecipitation and E12 for immunoblotting, from E Harlow (Mass General, Mass.); CDK2 mouse monoclonal PSTAIRE antibody, a gift from S. Reed (The Scripps Research Institute, Calif.); p27 mouse monoclonal antibody from Transduction Laboratories (Lexington, Ky.); and p21 rabbit polyclonal antibody from Santa Cruz Biotechnology, Cedarlane, Calif., α Brdu-FITS conjugate.

Vitamin E Causes $G_1$ Arrest In LNCaP and $G_2/M$ in PC3

Figure 1A:
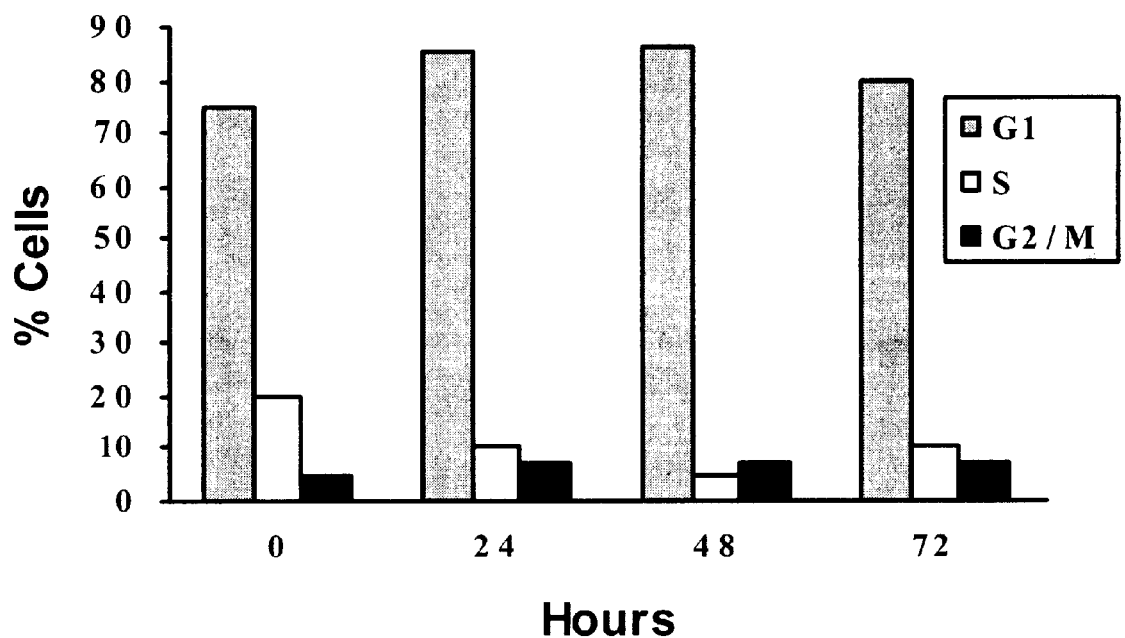
FIGS. 1*a* & *b*
Figure 1B:
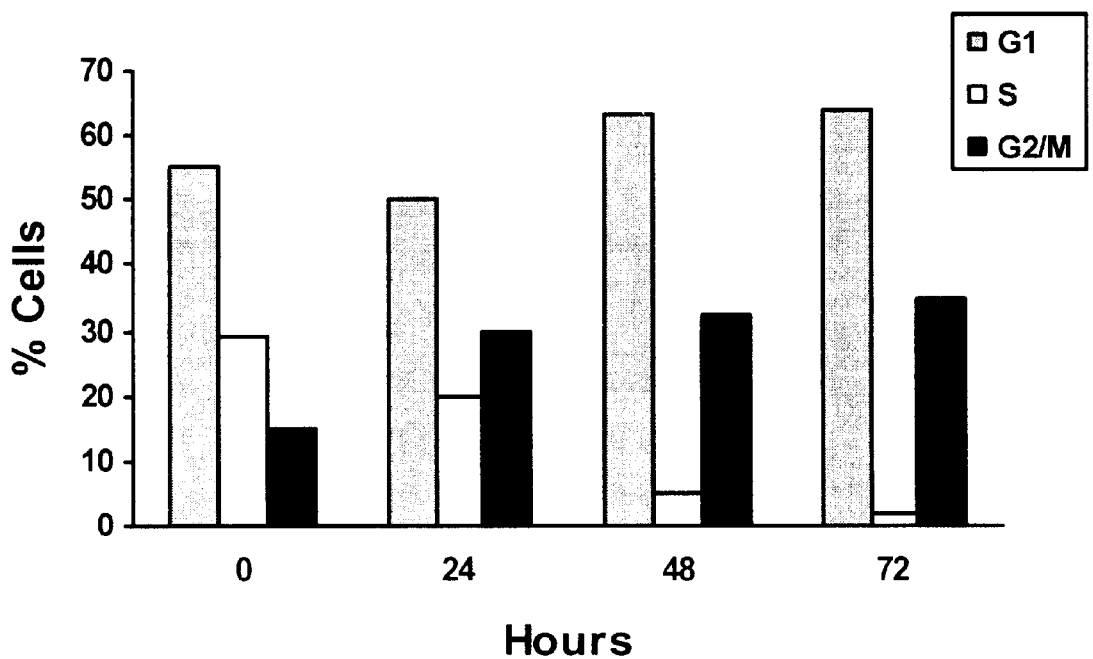

The results of this experiment produced cell cycle arrest in three of the four cell culture media. Treatment of asynchronously growing LNCaP and PC3 cells with Vitamin E for up to 72 hours induced a $G_1$ arrest of LNCaP and $G_2/M$ arrest of PC3 as early as 24 hours after treatment as demonstrated by DNA content histograms from flow cytometric studies. Between 24–72 hours of Vitamin E treatment, the significantly increased cell population in $G_2/M$ phase was associated with decreased cell numbers in S phase, as observed in PC3. After 24 hours, the percent reduction of cells in S phase was 49.5% (FIG. 1a) and 37.3% (FIG. 1b) in LNCaP and PC3, respectively. The cell arrest persisted for 72 hours in media supplemented with Vitamin E reducing the cells in the S phase by a maximum of 69.6% and 95.0% in LNCaP and PC3, respectively (Table 1).

There was no cytotoxicity as seen by their morphological appearance. No growth arrest was observed in the controls that were treated with the vehicle alone.

TABLE 1

| INHIBITORY EFFECT OF VITAMIN E | | | |
|---|---|---|---|
| | % Reduction S Phase | | |
| | 24 | 48 | 72 |
| Cell Line | | (Hours) | |
| LNCaP | 49.5 | 69.6 | 47.3 |
| PC3 | 37.3 | 82.8 | 95.0 |

Figure 2B:
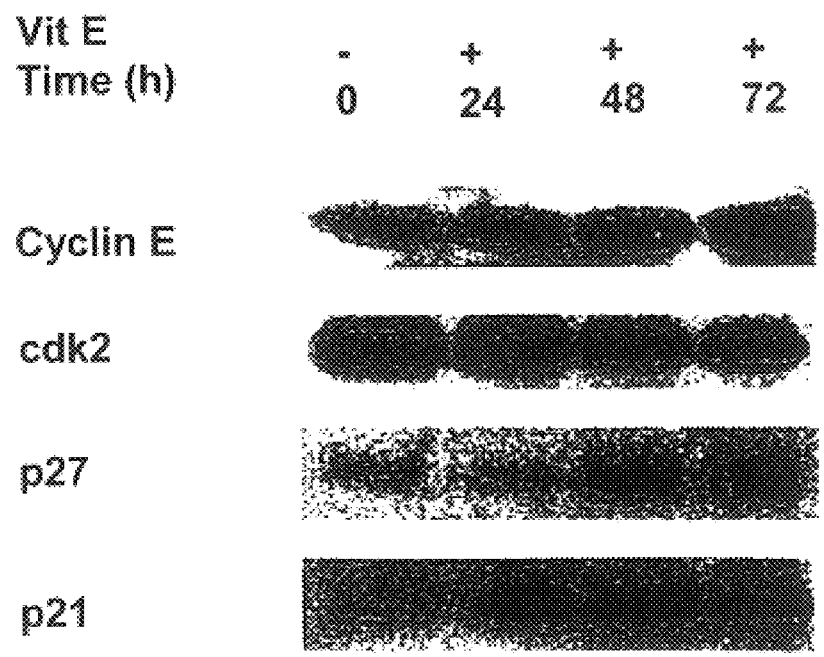

Alteration of p21 and p27 During Vitamin E Induced Cell Arrest p21, a cyclin-dependent kinase inhibitor, is known to be involved in $G_2/M$ phase arrest. The flow cytometry data (FIG. 1b) demonstrates that although Vitamin E arrested both cell lines, it did so at the $G_2/M$ phase of PC3. Thus to further investigate whether p21 is also implicated in Vitamin E induced inhibition of prostate cancer cell growth, p21 levels were examined in both LNCaP and PC3 cells following exposure to Vitamin E. There was no significant alteration in the levels of p21 in LNCaP (FIG. 2a), however, p21 levels were significantly upregulated in PC3 (FIG. 2b). This elevation in the levels of p21 was seen as early as 24 hours of treatment.

Inhibition of cyclin E/CDK2 activity was observed within 24 hours after treatment with Vitamin E. To determine whether the increase in p27 was sufficient to target cyclin E/cdk2 and induce cell cycle arrest, p27 was immunodepleted by three serial immunoprecipitations from both control and Vitamin E treated LNCaP cell lysates. Cyclin E immunecomplexes were examined before and after p27 immunodepletion. p27 immunodepletion caused a reduction in the cyclin E and cdk2 protein (FIG. 5). This shows a substantial proportion of the cells in the $G_1$ phase of the cell cycle.

Figure 3B:
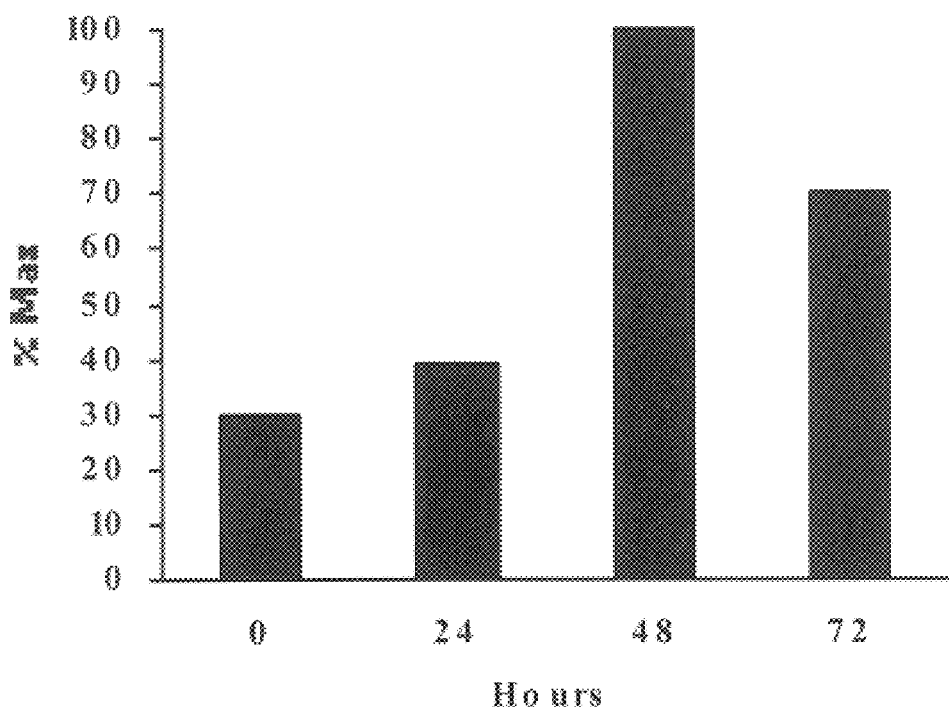
Figure 4B:
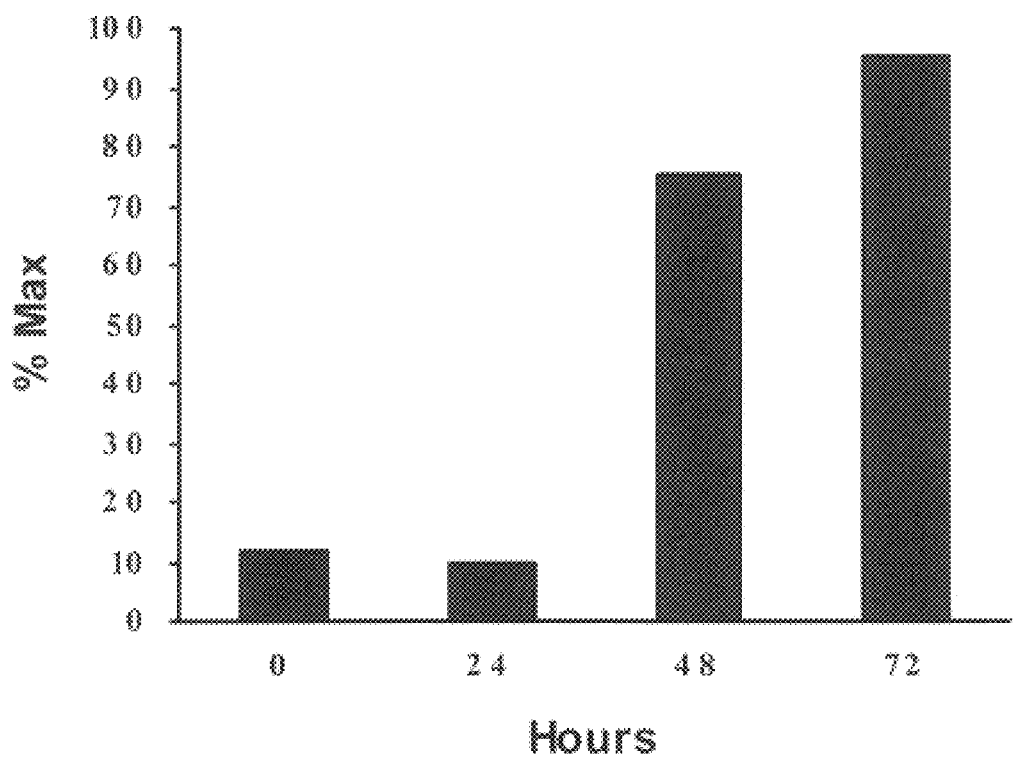
Figure 6A:
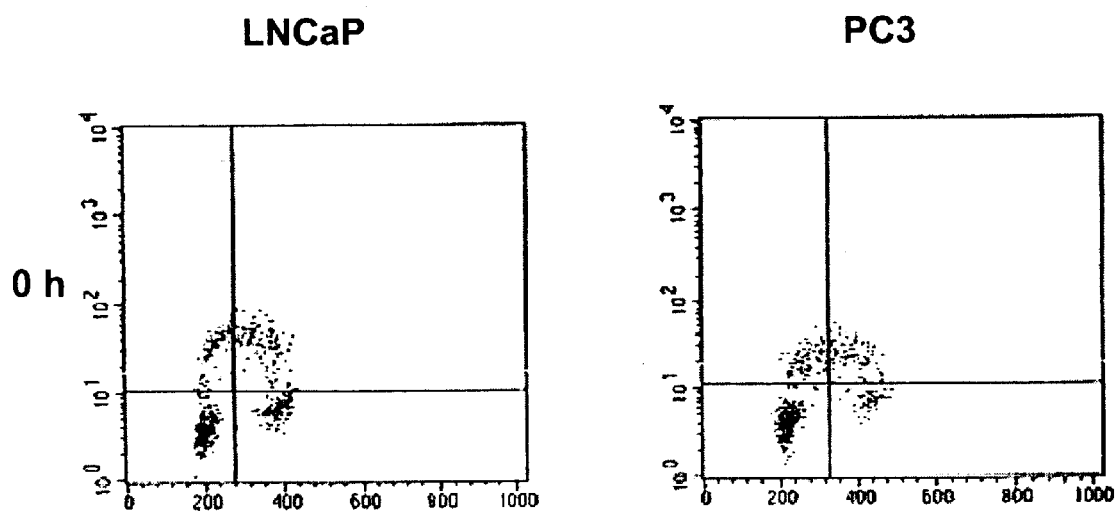
Figure 6B:
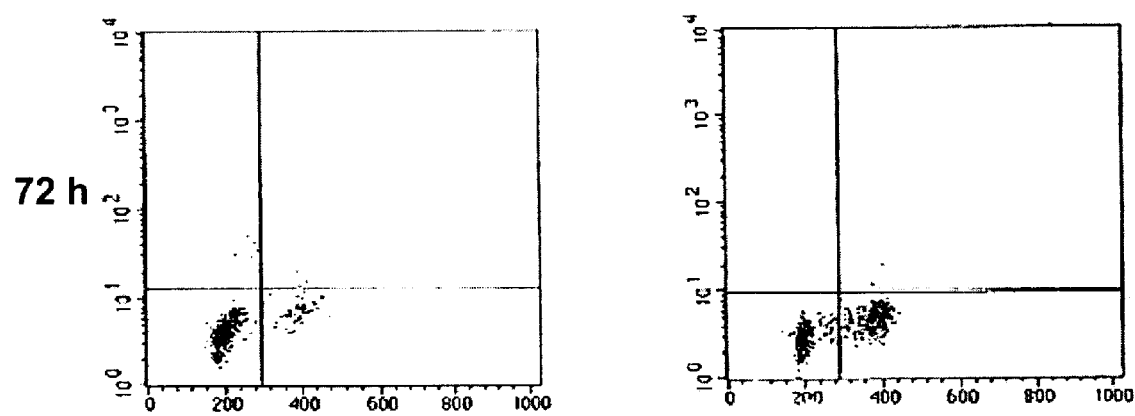

The LNCaP and PC3 cell lines show a characteristic bell shaped growth curve in response to Vitamin E (FIGS. 6a & 6b). The present study suggests that the increased level of p27 and its binding and inhibition of cyclin E/cdk2 contribute to $G_1$ arrest of LNCaP cells in response to Vitamin E. To look into the mechanism of inhibition of cyclin E/CDK2, these complexes were examined by immunoprecipitation of cyclin E followed by Western blotting to detect associated proteins (FIGS. 3a & 4a). In the Vitamin E-treated cell cultures, the amount of cyclin E-associated p27 in LNCaP increased 3-4 fold by densitometry (FIG. 3b), as the cells entered $G_1$ arrest. A similar increase was seen with the PC3 and detectable levels of p27 was seen 48 hours after treatment (FIG. 4b). Reports suggest that such an increase in p27 has been shown to saturate cyclin E/CDK2.

Selenium Causes $G_1$ Arrest of LNCaP with No Effect on PC3

Treatment of asynchronously growing LNCaP and PC3 cells with 30 μg/ml of selenium for up to 72 hours induced an arrest of LNCaP as early as 24 hours after treatment as demonstrated by DNA content histograms from flow cytometric studies (FIG. 7a). The percent reduction of cells in S phase was 58.1% by 24 hours of treatment. The cell arrest persisted for 72 hours in media supplemented with selenium reducing the cells in the S phase by a maximum of 80.3% (Table 2). There was no cytotoxicity as seen by their morphological appearance. No growth arrest was observed in controls treated with the vehicle alone. In contrast, treatment of PC3 showed no significant alteration in the number of cells in S phase even after 72 hours of treatment thereby indicating absence of growth arrest (8.4%) (FIG. 7b) (Table 2).

TABLE 2

INHIBITORY EFFECT OF SELENIUM

| Cell Line | % Reduction S Phase | | |
|---|---|---|---|
| | 24 | 48 (Hours) | 72 |
| LNCaP | 58.1 | 70.0 | 80.3 |
| PC3 | 3.6 | 6.9 | 8.4 |

Alteration of p21 and p27 Levels During Selenium Induced Cell Arrest p21, a cyclin-dependent kinase inhibitor, is known to be involved in $G_2/M$ phase arrest. Since there was a doubling of the number of cells in the $G_2/M$ phase, the present study investigated whether p21 is also implicated in selenium induced inhibition of prostate cancer cell growth. p21 levels were examined in both LNCaP and PC3 cells following exposure to selenium. p21 levels were significantly upregulated in LNCaP (FIG. 8a). This elevation in the levels of p21 was seen as early as 24 hours of treatment. There was no alteration in the levels of p21 in PC3 cells treated with selenium (FIG. 8b).

Inhibition of cyclin E/cdk2 activity was observed within 24 hours after treatment with selenium in LNCaP and PC3. To evaluate the mechanism of inhibition of cyclin E/cdk2, these complexes were examined by immunoprecipitation of cyclin E followed by western blotting to detect associated proteins (FIGS. 9 & 10). There was a 25% increase in the amount of cyclin E associated p27 in LNCaP as measured by densitometry (FIG. 9b) as the cells entered $G_1$ arrest. In contrast, PC3 cells treated with selenium behaved very differently than LNCaP in that cyclin E levels were increased by 72 hrs.

Results were different with the selenium-treated cell cultures than with Vitamin E. In these cultures, there was a 25% increase in the amount of cyclin E associated p27 in LNCaP as measured by densitometry as the cells entered $G_1$ arrest. In contrast, the cyclin E levels were increased by 72 hrs in the PC3 cell culture. The PC3 cell culture showed no detectable levels of p27 until the end of the treatment period; the two distinct bands of CDK2 on SDS-PAGE was seen only by 72 hrs.

It is therefore postulated that the increased p21 and p27, and their binding and inhibition of cyclin E/CDK2, play a role in inhibiting cell proliferation as regenerating prostatic tissue undergoes differentiation.

Research thus suggests that the increased level of p27 contributes to $G_1$ arrest of LNCaP human prostate carcinoma cells in response to Vitamin E, and that the increased level of p21 contributes to $G_2/M$ arrest of PC3 prostate cancer cells in response to Vitamin E. The antiproliferative effect of selenium on the two cell lines is different: there was no growth inhibition in the androgen-independent PC3 cells as compared to the marked reduction in the S-phase of the androgen-dependent LNCaP due to the increased levels of p21. This can be attributed to the fact that selenium may be mediating its effect through the androgen receptor and not due to the cell proliferating speed. Although little is known as to whether the androgen receptor also binds directly to the components of the cell cycle machinery and how such an interaction might modulate the transactivational activity of the receptor in prostate cancer, estrogens and androgens regulate the activity of CDKs by modulating the expression of cyclins or CDK-inhibitors, thereby promoting progression through the $G_1$-S transition of the cell cycle.

Evidence of the Enhanced Effects Using Vitamin E and Selenium

Figure 11:
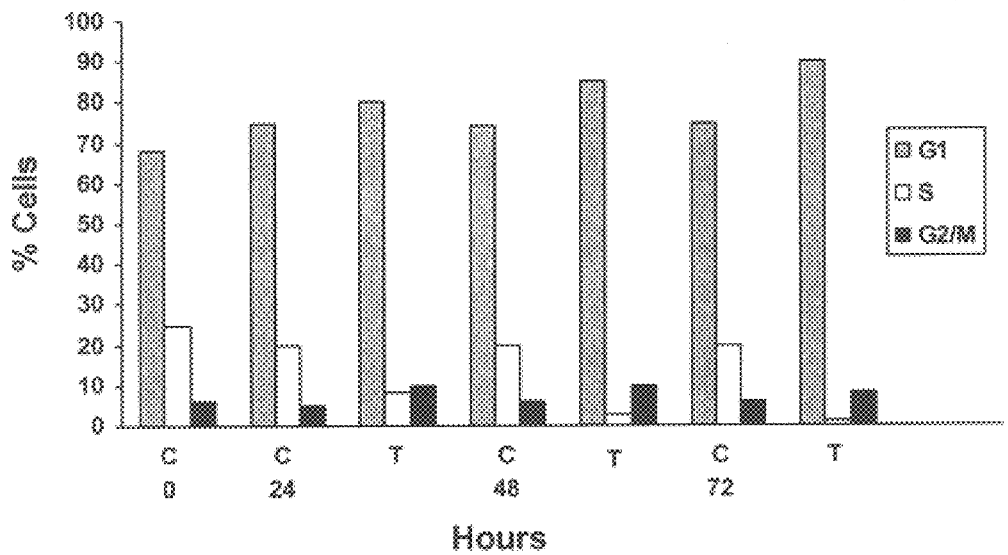
Figure 12:
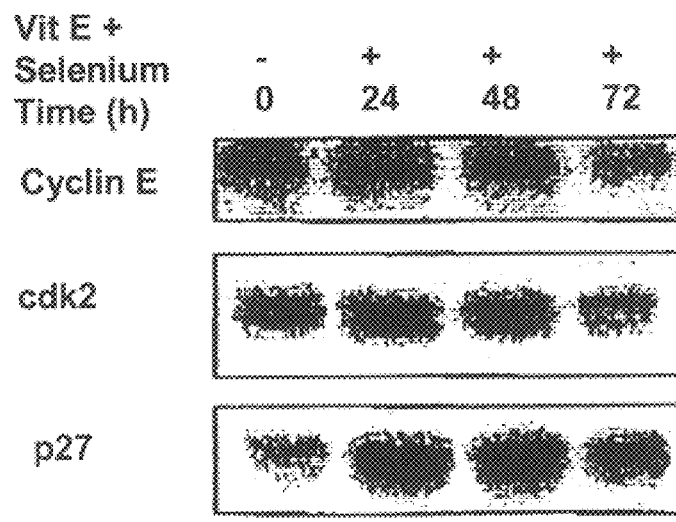

FIGS. 11 and 12 show the synergistic cell-cycle effects of using Vitamin E and selenium in combination. When LNCaP cells were treated with a combination of Vitamin E and selenium, the cell-cycle was arrested more significantly than with either agent alone. At 48 and 72 hours, S-phase was reduced to 4% and 1%, respectively, with concommittent increases in both $G_1$ and $G_2/M$ components. This resulted in a 63.1, 84.2 and 94.7% reduction in S phase at 24, 48 and 72 hours, respectively, compared to controls (Table 3). This data suggests that the anticancer properties by which these agents work are sufficiently different such that synergistic effects are realized if both are presented to the cell.

TABLE 3

INHIBITORY EFFECT OF SELENIUM AND VITAMIN E

| Cell Line | % Reduction S Phase | | |
|---|---|---|---|
| | 24 | 48 (Hours) | 72 |
| LNCaP | 63.1 | 84.2 | 94.7 |

Vitamin E is a fat-soluble vitamin found in cereal grains and leafy vegetables which, besides the anti-cancer properties listed herein, also prevents the oxidation of unsaturated fatty acids in such locations as the cell membrane, thereby helping maintain its structure. It may be ingested either as α-tocopherol or an α-tocopherol ester such as tocopherol succinate. Selenium is a trace element which may be ingested in such forms as sodium selenite or selenomethionine.

The composition may be taken orally, either as a capsule, a food additive, or as a meal rich in both constituents. Alternatively, these anti-cancer agents may be introduced into the bloodstream by hypodermic syringe.

The components of the composition can be administered together or separately. Administration of the composition may be parenteral, oral, intravenous, rectal, intrapleural, intrathecal, intraperitoneal, aerosol, or transdermal administration to achieve the desirable preventive or therapeutic effect. When administered orally, the composition may be in the form of tablets (single or multiplayer, coated or uncoated), capsules, or dragees. These oral formulations may be admixed with a solid excipient such as lactose, sucrose, starch, microcrystalline cellulose, magnesium sterate, or talc. When parenteral administration may be indicated, an aqueous solution or oleaginous formulation of the agent may be employed. Aqueous solutions can be prepared in water, physiological saline, or Ringer's solution, either with or without buffers. Oleaginous formulation may be made, for example, in natural oils (as in peanut oil or olive oil) or in benzyl benzoate.

The actual dosage amount administered can be determined by physical and physiological factors such as the activity of the specific compound employed; the age, body weight, general health, diet, time of administration, route of administration, rate of excretion, possible drug combination, and the idiopathy and the severity of condition of the patient or consumer. Clinically safe and effective dosages for the compounds with which the invention is concerned will be determined by clinical trials, as is required by the regulatory authorities in the art.

Furthermore, other chemical compounds safe for human consumption which increase the intracellular levels of p21 and p27, and thereby increase the inhibition of cyclin-CDK complexes, are available for use as anti-cancer agents.

Vitamin E is not a single entity. It is a term that describes a family of related compounds called tocopherols and tocotrienols. See Brigelius-Flohe R, Traber M G, "Vitamin E: Function and Metabolism," *FASEB* (1999) 13:1145–1155. There are 4 tocopherols and 4 tocotrienols: alpha, beta, gamma, and delta, respectively (FIG. 13). Alpha-tocopherol is the most abundant natural form of Vitamin E, representing approximately 90% of tocopherols in most mammalian tissues. It has the highest biological activity and reverses Vitamin E deficiency in humans. See Traber M G, Arai H, "Molecular Mechanisms of Vitamin E Transport," *Annu Rev Nutr* (1999) 19:343–55.

There are three chiral centers in the tocopherol family that determines their stereospecificity. Natural forms (predominantly plant derived) of α-tocopherol are exclusively in the all-dextro (RRR) isomer. Vitamin E supplements however can contain either natural RRR (d-α-tocopherol) or synthetic Vitamin E. Synthetic forms of Vitamin E, also known as all rac α-tocopherol (or dl-α-tocopherol), contains all 8 possible stereoisomers. See Brigelius-Flohe R, Traber M G, "Vitamin E: Function and Metabolism," *FASEB* (1999) 13:1145–1155. The bioactivities of these compounds are not identical. As a general rule, using synthetic dl-α-tocopherol as a standard, d-α-tocopherol (natural form) would possess 1.49 times its bioactivity. See Pryor W A, "Vitamin E and Heart Disease: Basic Science to Clinical Intervention Trials," *Free Radic Biol Med* (Jan. 1, 2000) 28(1):141–64.

Commercially available Vitamin E comes in either an esterified or unesterified form. All esterified forms of natural Vitamin E have similar bioactivity. Conversion of milligrams to international units depends on the formulation of Vitamin E. In general, 1 IU equals the activity of 1 mg of dl-α-tocopherol acetate (i.e. synthetic form). There are a variety of reasons explaining the variation in bioactivity of the various forms of Vitamin E including: 1) distinct biologic activities of the isomers themselves; See Brigelius-Flohe R, Traber M G, "Vitamin E: Function and Metabolism," *FASEB* (1999) 13:1145–1155; 2) different rates or modes of transport; 3) existence of specific transport mechanisms for RRR-α-tocopherol; See Traber M G, Arai H, "Molecular Mechanisms of Vitamin E Transport," *Annu Rev Nutr* (1999) 19:343–55; and 4) specific interactions of various isomers with receptors; See Traber M G, Arai H., "Molecular Mechanisms of Vitamin E Transport," *Annu Rev Nutr* (1999) 19:343–55.

Vitamin E is ingested orally either via foods or nutritional supplements. Good dietary sources of Vitamin E tend to represent foods rich in plant derived oils including: avocados, nuts, eggs, peanut butter, soybeans and ready-to-eat whole-grain breakfast cereals. Cooking oils tend to be the largest source of Vitamin E in the diet. See Rao A V, Fleshner N, Agarwal S. Rao A V, Fleshner N, Agarwal S., *Nutr Cancer* (1999) 33(2):159–64.

Recommended daily allowance of Vitamin E is 10 mg/day. This amount is normally met by dietary sources for those individuals who consume a healthy diet. However diet alone may not supply the amounts required to prevent chronic diseases. This is particularly true if a low-fat dietary plan is desirous. A meal rich in Vitamin E poses problems because Vitamin E is fat soluble and therefore is found in fats. Ideally then increased Vitamin E intake is best achieved through supplementation.

Once ingested, Vitamin E is absorbed via intestinal lymphatics along with medium chain fatty acids. It is then packed into chylomicrons and transported to the liver. Once passed through the liver, α-tocopherol appears to be preferentially secreted into the plasma. The α-Tocopherol Transfer Protein (α-TTP), a specific liver protein, is responsible for this preference. See Azzi A, Breyer I, Feher M, Pastori M, Ricciarelli R, Spycher S, Staffieri M, Stocker A, Zimmer S, Zingg J M, "Specific Cellular Responses to Alpha-Tocopherol," *J Nutr* (July 2000) 130(7):1649–52. The β-, δ-, and γ-tocopherol forms are mostly secreted into the bile and excreted via the feces. Plasma levels of Vitamin E are saturable at a level of 80 μM; levels in excess of 80 μM are unachievable with Vitamin E megadosing. Approximately 800 IU's per day are required to achieve saturable levels in the blood. See Brigelius-Flohe R, Traber M G, "Vitamin E Function and Metabolism," *FASEB* (1999) 13:1145–1155.

Unless defined otherwise, all technical and scientific terms used herein have the same meaning as commonly understood by one of ordinary skill in the art to which this invention belongs. Although any methods and materials similar or equivalent to those described can be used in the practice of testing the present invention, the preferred methods and materials are now described. All publications and patent documents referenced in this application are incorporated herein by reference in their entirety as though each and every publication and patent document was specifically incorporated herein by reference in its entirety.

The present invention is not to be limited in scope by any embodiments disclosed which are intended as an illustration of one aspect of the invention, nor by any methods which are functionally equivalent to the scope of the invention. Indeed, various modifications of the invention in addition to those shown and described herein will become apparent to those skilled in the art from the foregoing description. Such modifications are intended to fall within the scope of the appended claims.

The invention to be claimed is:

1. A method of preventing or treating mammalian prostate carcinoma in a subject comprising administration to a subject in need of such prevention or treatment an effective amount of a nutrient supplement composition consisting essentially of Vitamin E, or a Vitamin E derivative or Vitamin E analog and selenium or a selenium salt or selenium derivative either in combined or uncombined form.

2. The method of claim 1, wherein said Vitamin E or Vitamin E derivative or Vitamin E analog is in the form of a tocopherol or a tocopherol derivative or analog or a tocotrienol or derivatives or analogs thereof.

3. The method of claim 1, wherein said selenium or a selenium salt or selenium derivative is in the form of selenite salt, selenomethionine, selenium yeast, selenium oxide or a selenium acid and mixtures thereof.

4. The method of claim 1, wherein said administered composition is in a form suitable for oral, parenteral, intraperintoneal, intravenous, rectal, intrapleural, intrathecal, aerosol or transdermal administration.

5. The method of claim 1, wherein said administered composition is in the form of a food additive.

6. The method of claim 1, wherein said administered composition is in an injectable form.

7. The method of claim 1, wherein the composition is a dosage form containing a mixture of Vitamin E or Vitamin E derivative or Vitamin E analog and selenium or a selenium salt or selenium derivative or a dosage form wherein Vitamin E or Vitamin E derivative or Vitamin E analog and selenium or a selenium salt or selenium derivative can be separately administered.

8. The method of claim 1, wherein the administration comprises administering Vitamin E or Vitamin E derivative or Vitamin E analog and selenium or a selenium salt or selenium derivative either together or separately.

9. A method of preventing or treating mammalian prostate carcinoma in a subject by increasing intracellular levels of p21 and/or p27 comprising administration to a subject in need of such prevention or treatment an effective amount of a composition, said composition consisting essentially of a combination of Vitamin E or a Vitamin E derivative or Vitamin E analog and selenium or a selenium salt or selenium derivative in combined or uncombined form, wherein said composition is effective to increase the intracellular levels of p21 and/or p27.

10. The composition as claimed in claim 9, wherein the Vitamin E, Vitamin E derivative or Vitamin E analog, is in the form of a tocopherol or a tocopherol derivative or analog or tocotrienol or derivatives or analogs thereof and mixtures thereof.

11. The composition as claimed in claim 9, wherein the selenium or selenium salt or selenium derivative is in the form of a selenite salt, selenomethionine, selenium yeast, selenium oxide or a selenium acid and mixtures thereof.

12. The method as claimed in claim 9, wherein the composition is in a form suitable for oral, parenteral, intravenous, intraperitoneal, rectal, intrapleural, intrathecal, aerosol or transdermal administration.

13. The method as claimed in claim 9, wherein the composition is in a dosage form combining a mixture of Vitamin E or Vitamin E derivative or Vitamin E analog and selenium or a selenium salt or selenium derivative or a dosage form wherein Vitamin E or Vitamin E derivative or Vitamin E analog and selenium or a selenium salt or selenium derivative can be separately administered.

14. The method as claimed in claim 9, wherein the administration comprises administering Vitamin E or Vitamin E derivative or Vitamin E analog and selenium or a selenium salt or selenium derivative either together or separately.

15. The method as claimed in claim 9, wherein said administered composition is in the form of a food additive.

16. The method as claimed in claim 9, wherein said administered composition is in an injectable form.

* * * * *

UNITED STATES PATENT AND TRADEMARK OFFICE
CERTIFICATE OF CORRECTION

| | | |
|---|---|---|
| PATENT NO. | : 6,670,392 B2 | Page 1 of 1 |
| APPLICATION NO. | : 09/828405 | |
| DATED | : December 30, 2003 | |
| INVENTOR(S) | : Neil E. Fleshner | |

It is certified that error appears in the above-identified patent and that said Letters Patent is hereby corrected as shown below:

Col. 12, line 21 and Col. 12, line 26
In claims 10 and 11 replace "composition" with --method.--

Signed and Sealed this

Twenty-fifth Day of December, 2007

JON W. DUDAS
*Director of the United States Patent and Trademark Office*